(12) United States Patent
Gelb et al.

(10) Patent No.: US 10,281,741 B2
(45) Date of Patent: May 7, 2019

(54) OPHTHALMIC LENS TREATMENT SYSTEM (71) Applicant: ESSILOR INTERNATIONAL (COMPAGNIE GENERALE D'OPTIQUE), Charenton le Pont (FR)

(72) Inventors: Brad Gelb, Dallas, TX (US); Mark Hale, Dallas, TX (US); Mark Mildebrath, Dallas, TX (US)

(73) Assignee: ESSILOR INTERNATIONAL, Charenton-le-Pont (FR)

( * ) Notice: Subject to any disclaimer, the term of this patent is extended or adjusted under 35 U.S.C. 154(b) by 0 days.

(21) Appl. No.: 15/538,593

(22) PCT Filed: Dec. 23, 2014

(86) PCT No.: PCT/IB2014/003130
§ 371 (c)(1),
(2) Date: Jun. 21, 2017

(87) PCT Pub. No.: WO2016/102998
PCT Pub. Date: Jun. 30, 2016

(65) Prior Publication Data
US 2017/0348928 A1 Dec. 7, 2017

(51) Int. Cl.
G02C 7/02 (2006.01)
B29D 11/00 (2006.01)
A61F 2/16 (2006.01)

(52) U.S. Cl.
CPC ........ *G02C 7/028* (2013.01); *B29D 11/00009* (2013.01); *B29D 11/00923* (2013.01); *B29D 11/00961* (2013.01); *A61F 2/16* (2013.01)

(58) Field of Classification Search
CPC .......... G02C 7/024; G02C 7/02; G02C 7/028; G02C 7/04; B29D 11/00923;
(Continued)

(56) References Cited

U.S. PATENT DOCUMENTS

2006/0065989 A1* 3/2006 Druffel ............... B29C 35/0805
264/1.32
2010/0047380 A1* 2/2010 Widman .......... B29D 11/00009
425/174.4

(Continued)

FOREIGN PATENT DOCUMENTS

EP 2604414 6/2013
WO WO 2014/177387 11/2014

*Primary Examiner* — Jordan M Schwartz
(74) *Attorney, Agent, or Firm* — Norton Rose Fulbright US LLP (57) ABSTRACT An ophthalmic lens treatment planning System receives lens and ophthalmic lens treatment information from a customer lens order, identification of available equipment to apply ophthalmic lens treatment(s) from the customer order, and performance and parameters of the available equipment. The ophthalmic lens treatment planning System formulates an optimal ophthalmic lens treatment plan to be implemented by the available equipment to apply the ophthalmic lens treatment(s) from the customer order to the lens. Following application of the optimal ophthalmic lens treatment plan to the lens, the resulting lens may be measured to provide last run results and the last run results may be fed back to the ophthalmic lens treatment planning System to provide further performance and parameters of the available equipment to the ophthalmic lens treatment planning System.

12 Claims, 3 Drawing Sheets (58) Field of Classification Search
CPC ........ B29D 11/00951; B29D 11/00961; B29D 11/00048; G02B 1/041
See application file for complete search history.

(56) References Cited

U.S. PATENT DOCUMENTS

| | | |
|---|---|---|
| 2013/0084778 A1 | 4/2013 | Lavrador et al. |
| 2015/0277418 A1* | 10/2015 | Arrigotti .............. G05B 19/182 700/103 |
| 2015/0328740 A1* | 11/2015 | Gacoin ............... B24B 13/0055 451/5 |
| 2016/0161760 A1* | 6/2016 | Godot .............. B29D 11/00961 351/159.69 |

\* cited by examiner

OPHTHALMIC LENS TREATMENT SYSTEM

CROSS-REFERENCE TO RELATED APPLICATIONS

This application is a national phase application under 35 U.S.C. § 371 of International Application No. PCT/IB2014/003130 filed 23 Dec. 2014, the entire contents of which is specifically incorporated by reference herein without disclaimer.

TECHNICAL FIELD

The present disclosure relates generally to ophthalmic lens treatment application, more particularly to systems and methods for optimizing the selection and application of ophthalmic lens treatments, and specifically to systems and methods for optimizing a ophthalmic lens treatment plan by considering the equipment used to process and treat the lens(es) and/or by taking into account the results of previous treatments.

BACKGROUND

Ophthalmic lens treatments may include, but are not necessarily limited to, coatings, tints, films, polarization, photochromic properties, and other techniques for applying treatments to lenses. Ophthalmic lenses are typically treated using batch processes, thus limiting the optimization of the performance of the treatments applied to a particular lens or pair of lenses. Such batch processing typically employs a best acceptable average application of such treatments, thereby providing each individual lens or pair of lenses, at best, a compromise lens treatment.

SUMMARY

The present invention is directed to systems and methods which provide various implementations that call for receiving, such as in an ophthalmic lens treatment planning system, lens and ophthalmic lens treatment information from a customer lens order, receiving identification of available equipment to apply ophthalmic lens treatment(s) from the customer order, and receiving performance and parameters of the available equipment. Whereupon, the ophthalmic lens treatment planning system, formulates an optimal ophthalmic lens treatment plan to be implemented by the available equipment used to apply the ophthalmic lens treatment(s) from the customer order to the lens. In accordance with various embodiments of the present systems and methods, formulation of an optimal ophthalmic lens treatment plan to be implemented by the available equipment to the lens further may include applying computer-based models to the plan employing possible combinations of ophthalmic lens treatments that can be applied to the lens employing the available equipment. In various implementations formulating an optimal ophthalmic lens treatment plan may include considering aspects of a given lens or pair of lenses relevant to ophthalmic lens treatments for the given lens or pair of lenses, including the available equipment and performance and parameters of the available equipment, and considering and optimizing the optimal ophthalmic lens treatment plan for the available equipment and performance and parameters of the available equipment. In accordance with some embodiments of the present systems and methods, the optimal ophthalmic lens treatment plan may include application of some ophthalmic lens treatment(s) using a batch process.

Following application of the optimal ophthalmic lens treatment plan to the lens, the resulting lens may be measured to provide last run results. The last run results may be fed back to the ophthalmic lens treatment planning system to provide further performance and parameters of the available equipment to the ophthalmic lens treatment planning system. Such last run results may include a measure of lens spectral performance including reflection, transmission and absorption characteristics as well as spectral parameters, product performance testing, cosmetic inspection, treatment adhesion, scratch resistance, abrasion resistance, and/or chemical resistance.

In accordance with various embodiments of the present systems and methods, the ophthalmic lens treatment(s) may include an anti-reflective coating, and formulating an optimal ophthalmic lens treatment plan may include optimizing anti-reflective coating thicknesses, application rates, ramps, soaks, ion gun power, gas flows, gas pressure, electron beam gun voltage, distribution mask size, distribution mask location, lens fixture and/or application process for the available equipment and the performance and parameters of the available equipment.

The ophthalmic lens treatment information may include information about lens coatings, lens tints, lens films, lens polarization, lens photochromic properties, information about techniques for applying treatments to the lens, information about hard multicoat lens treatments, and/or the like. The performance and parameters of the available equipment may include use of an electron beam gun, any sputter target employed for deposition of coatings, use of evaporation boats, use of an ion gun, condition of filaments, condition of specific components within the electron beam gun or the ion gun, use of shields, cleanliness of shields, use of distribution masks, sector geometry employed by the available equipment, resulting optical thickness measurement, resulting lens axis orientation, resulting lens color, age of coating material to be used, condition of tooling, age of chemicals to be used, condition of chemicals to be used, age of dye bath, dye bath temperature, and/or room conditions for the available equipment.

In accordance with various embodiments of the present systems and methods, the ophthalmic lens treatment(s) may include a hard coating, and formulating an optimal ophthalmic lens treatment plan may include optimizing hard coating thickness, type, cure rate, cure type, tooling, lens preparation process, lens stripping process and/or treatment application process for the available equipment and the performance and parameters of the available equipment.

In accordance with various embodiments of the present systems and methods, the ophthalmic lens treatment(s) may include tinting, and formulating an optimal ophthalmic lens treatment plan may include optimizing tinting temperature, color, dye(s) to use, time, pre-processing, post-processing, gradient parameters, dye application processes and/or the like, for the available equipment and the performance and parameters of the available equipment.

Hence, in accordance with embodiments herein an ophthalmic lens treatment system may incorporate equipment available to ophthalmic lens treatment(s) and an ophthalmic lens treatment planning system. This ophthalmic lens treatment planning system may be configured to receive lens and ophthalmic lens treatment information from a customer lens order, receive identification of the equipment available, and receive performance and parameters of the equipment available. The ophthalmic lens treatment planning system may formulate an optimal ophthalmic lens treatment plan to be implemented by the available equipment to apply one or more ophthalmic lens treatments from the customer lens order to the lens. The ophthalmic lens treatment planning system may be further configured to accept measurements of a resulting lens, following application of the optimal ophthalmic lens treatment plan to the lens, to develop last run results. Such last run results may then be fed back to the ophthalmic lens treatment planning system to provide further performance and parameters of the available equipment to the ophthalmic lens treatment planning system.

In various embodiments, one or more of the techniques described herein may be performed by one or more computer systems. In other various embodiments, a tangible computer-readable storage medium may have program instructions stored thereon that, upon execution by one or more computer systems, cause the one or more computer systems to execute one or more operations disclosed herein. In yet other various embodiments, one or more systems may each include at least one processor and memory coupled to the processors, wherein the memory is configured to store program instructions executable by the processor(s) to cause the system(s) to execute one or more operations disclosed herein.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

Having thus described the invention in general terms, reference will now be made to the accompanying drawings, which are incorporated in and form part of the specification and in which like numerals designate like parts, illustrate embodiments of the present invention and together with the description, serve to explain the principles of the invention. In the drawings:

While this specification provides several embodiments and illustrative drawings, a person of ordinary skill in the art will recognize that the present specification is not limited only to the embodiments or drawings described. It should be understood that the drawings and detailed description are not intended to limit the specification to the particular form disclosed, but, on the contrary, the intention is to cover all modifications, equivalents and alternatives falling within the spirit and scope of the claims. As used herein, the word "may" is meant to convey a permissive sense (i.e., meaning "having the potential to"), rather than a mandatory sense (i.e., meaning "must"). Similarly, the words "include," "including," and "includes" mean "including, but not limited to."

DETAILED DESCRIPTION

The invention now will be described more fully hereinafter with reference to the accompanying drawings. This invention may, however, be embodied in many different forms and should not be construed as limited to the embodiments set forth herein. Rather, these embodiments are provided so that this disclosure will be thorough and complete, and will fully convey the scope of the invention to those skilled in the art. One skilled in the art may be able to use the various embodiments of the invention.

As noted, the present disclosure relates generally to ophthalmic lens treatment application and more particularly to systems and methods for optimizing the selection and application of ophthalmic lens treatments. Specific embodiments discussed herein relate to systems and methods for optimizing an ophthalmic lens treatment plan by considering the equipment and equipment configurations used to process and treat the lens(es) and/or by taking into account the results of previous treatments. In accordance with embodiments of the present systems and methods, an ophthalmic lens treatment planning system receives lens and ophthalmic lens treatment information from a customer lens order, identification of available equipment to apply ophthalmic lens treatment(s) from the customer order, and performance and parameters of the available equipment. The ophthalmic lens treatment planning system formulates an optimal ophthalmic lens treatment plan to be implemented by the available equipment to apply the ophthalmic lens treatment(s) from the customer order to the lens. Following application of the optimal ophthalmic lens treatment plan to the lens, the resulting lens may be measured to provide last run results and the last run results may be fed back to the ophthalmic lens treatment planning system to provide further performance and parameters of the available equipment to the ophthalmic lens treatment planning system.

Figure 1:
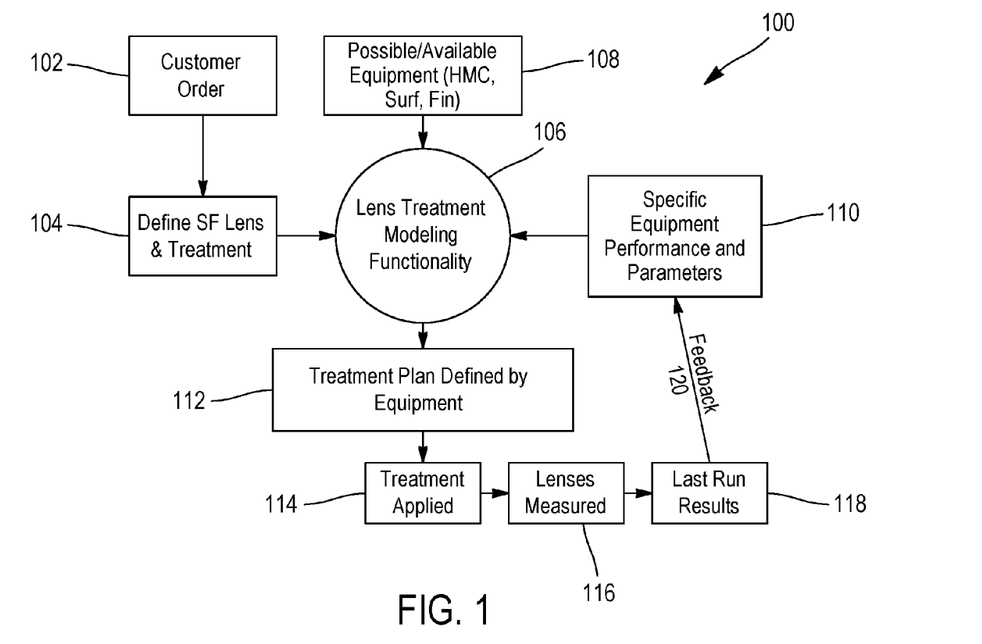
FIG. 1 is a block diagram of an embodiment of an example ophthalmic lens treatment planning system and process overview, according to various embodiments.

Embodiments of the present systems and methods, employ computer-based models that consider relevant specific aspects of a given lens or pair of lenses. These models optimize the selection of and application of ophthalmic lens treatments. In particular, these models may consider not only the wearer needs but also the equipment used to process and treat the lens(es). Further, the present systems and methods may include an ability of these models to take into account the results of previous treatments in order to optimize the process and equipment to insure the correct result in subsequent treatments. As a result, these models may allow an eye care professional, lens laboratory, or other applicable provider to fully consider and optimize specific needs of a given lens or pair of lenses. Rather than target average output as with batching, the present systems and methods may be used to customize lenses to a greater degree for the wearer. Traditionally, it is not possible or practical to apply lens treatments at such a highly individualized level. Further, traditional systems cannot adjust processes and equipment, in real time, in order to account for process and equipment drifts such that each treatment application may be optimized based on the performance of recently applied treatments. Hence, the present systems and methods provide for personalization of lens treatments, while affording a lens laboratory automation for determining lens treating equipment settings. Use of the present computerized systems and methods gives a more optimized application of lens treatments, taking into account what resulted from the earlier application of similar treatments FIG. 1 is a block diagram of an overview of an embodiment of example ophthalmic lens treatment planning system and process 100, according to various embodiments. System and process 100 considers aspects of a given lens, or pair of lenses, relevant to ophthalmic lens treatments for the given lens or pair of lenses, including wearer needs and equipment to be used to process and treat the given lens or pair of lenses. Whereupon system and process 100 optimizes selection of and/or application of ophthalmic lens treatments for the given lens or pair of lenses and the equipment.

In the illustrated example, customer order 102's lens and ophthalmic lens treatment information 104 is received in lens treatment modeling functionality 106. Information 104 may include, by way of example, information about hard multi-coat lens treatments, such as information about lens coatings, lens tints, lens films, lens polarization, lens photochromic properties, as well as information about techniques for applying treatments to the lens, and further lens surfacing, or lens finishing, or the like. Identification of equipment available (or that may possibly be used) (108) for application of lens treatments (104) is provided to lens treatment modeling functionality 106. Modeling functionality 106 may in accordance with various embodiments of the present systems and methods, be computer-based and may take the form of a special purpose ophthalmic lens treatment planning system, at least a part of (a) centralized control system(s) for lens treatment equipment, software executing on a computer system, or the like. For example embodiments of the present systems and methods may be incorporated into, or be employed in conjunction with ophthalmic lens laboratory software such as may typically be referred to as a Lab Management System (LMS), a Lens Design System (LDS), or the like. Performance and parameters 110 of available equipment 108 is also provided to equipment modeling functionality 106. Modeling functionality 106 determines, and/or otherwise formulates, ophthalmic lens treatment application plan 112 to be applied by the equipment to the lens. That is, formulating and determining ophthalmic lens treatment plan 112 to be applied by the equipment 108 to the lens may include applying computer-based models to the lens treatment application plan, such as by modeling employment of possible combinations of ophthalmic lens treatments that can be applied to the lens using the available equipment 108. For example, formulating, or otherwise determining, an ophthalmic lens treatment plan may include considering aspects of a given lens or pair of lenses relevant to requested ophthalmic lens treatments for the given lens or pair of lenses, including the equipment available to apply ophthalmic lens treatments and performance and parameters of the equipment, and then considering and optimizing an ophthalmic lens treatment plan for the equipment available to apply ophthalmic lens treatments and performance and parameters of the equipment. Hence, lens treatment plan 112 may be defined by equipment 108 available to apply the lens treatments and the performance and parameters 110 of such equipment, in accordance with various embodiments of the present systems and methods.

In considering aspects of a given lens or pair of lenses relevant to ophthalmic lens treatments for the given lens or pair of lenses, embodiments of the present systems and methods may dynamically account for results of previous ophthalmic lens treatments. For example, as discussed in greater detail below, with reference to FIG. 3, following application of the ophthalmic lens treatment plan to the lens 114, the resulting lens may be measured at 116 to provide last run results 118. Whereupon, last run results 118 may be fed back at 120 to provide further performance and parameters 110 of the equipment to ophthalmic lens treatment modeling functionality 106

Figure 2:
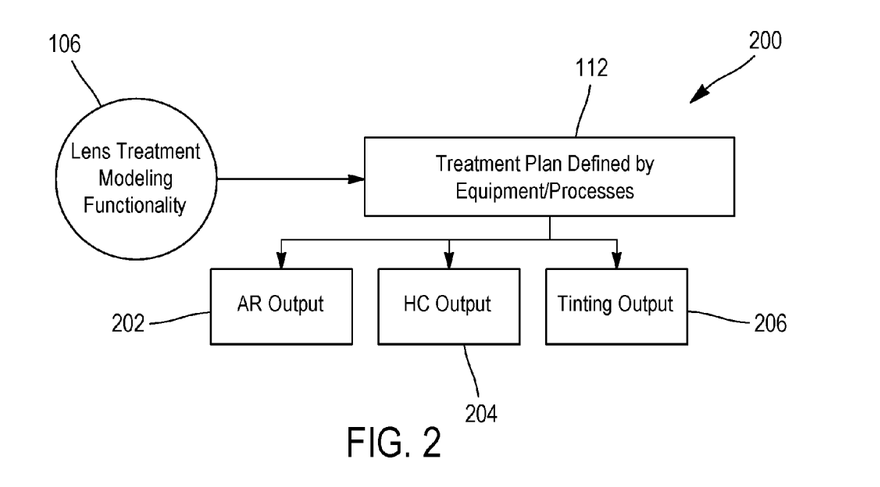
FIG. 2 is a block diagram of treatment plan output from, by way of example, the system and process of FIG. 1, shown as including a number of possible plan modeling outputs, according to various embodiments.

Returning to lens treatment plans 112, which may be, as noted, defined in light of the equipment available to apply the lens treatments and the performance and parameters of such equipment, attention is directed to FIG. 2. Wherein, a block diagram of treatment plan output 200 from, by way of example, system and process 100 of FIG. 1, is shown as including a number of possible plan modeling outputs 202 through 206, according to various embodiments. Therein, as discussed above, modeling functionality 106 formulates and outputs ophthalmic lens treatment plan 112, which is to be applied by the equipment to the lens, based at least in part on the equipment available to apply the ophthalmic lens treatments and/or the performance and parameters of the equipment. Lens treatment plan 112 may include (i.e. callout) a number of outputs, including, anti-reflective coating output 202, hard coating output 204, tinting output 206, and/or the like. In accordance with various embodiments of the present systems and methods, lens treatment modeling functionality 106 may also adjust outputs 202, 204, 206, etc. based on upstream and/or downstream processes and equipment, such as surfacing processes, finishing processes, and/or the like.

Where the ophthalmic lens treatments include an anti-reflective coating, formulation of ophthalmic lens treatment plan 112 may result in anti-reflective coating output 202. Formulation of anti-reflective coating output 202 may include optimizing any of a number of variable anti-reflective coating process parameters, such as, coating layer thicknesses, application rates, ramps, soaks, ion gun power, gas flows, and/or process pressure. Other anti-reflective coating application parameters related to specifications of equipment available to apply the ant-reflective treatment might also be taken into account, such as, e-gun voltage, available distribution mask size, distribution mask location(s), fixture(s) and/or the like. Thereby, an anti-reflective application process employing the equipment available to apply the ophthalmic lens treatments for lens and taking into account the performance and parameters of the available equipment may be optimized for the lens may be embodied in anti-reflective output 202.

Concurrently, where the ophthalmic lens treatments include a hard coating, formulation of ophthalmic lens treatment plan 112 may result in hard coating output 204. Determining hard coating output 204 may include optimizing any of a number of hard coating parameters, such as a hard coating thickness, type, cure rate, cure type, as well as available preparation and application equipment and tooling, available lens preparation process(es), lens stripping process(es) and/or the like for the available treatment application process(es). Thereby, a hard coating application process employing the equipment available to apply the ophthalmic lens treatments and taking into account the performance and parameters of the available equipment may be optimized for the lens as hard coating output 204.

Where the ophthalmic lens treatments include tinting, concurrent determination of an ophthalmic lens treatment plan 112 my result in tinting output 106. Formulation of tinting output 206 may include optimizing any number of tinting process parameters, such as temperature, color, one or more treatment dyes to use, time, or the like. Further, tinting output 206 may take into account or call for particular pre-processing, post-processing, tinting gradient parameters, or the like. Tint applicator parameters, and/or dye application processes employed by the equipment available may also be taken into account in tinting output 206. Thereby, a tinting process employing the equipment available to apply the ophthalmic lens treatments and taking into account the performance and parameters of the equipment may be optimized for the lens in the form of tinting output 206.

Figure 3:
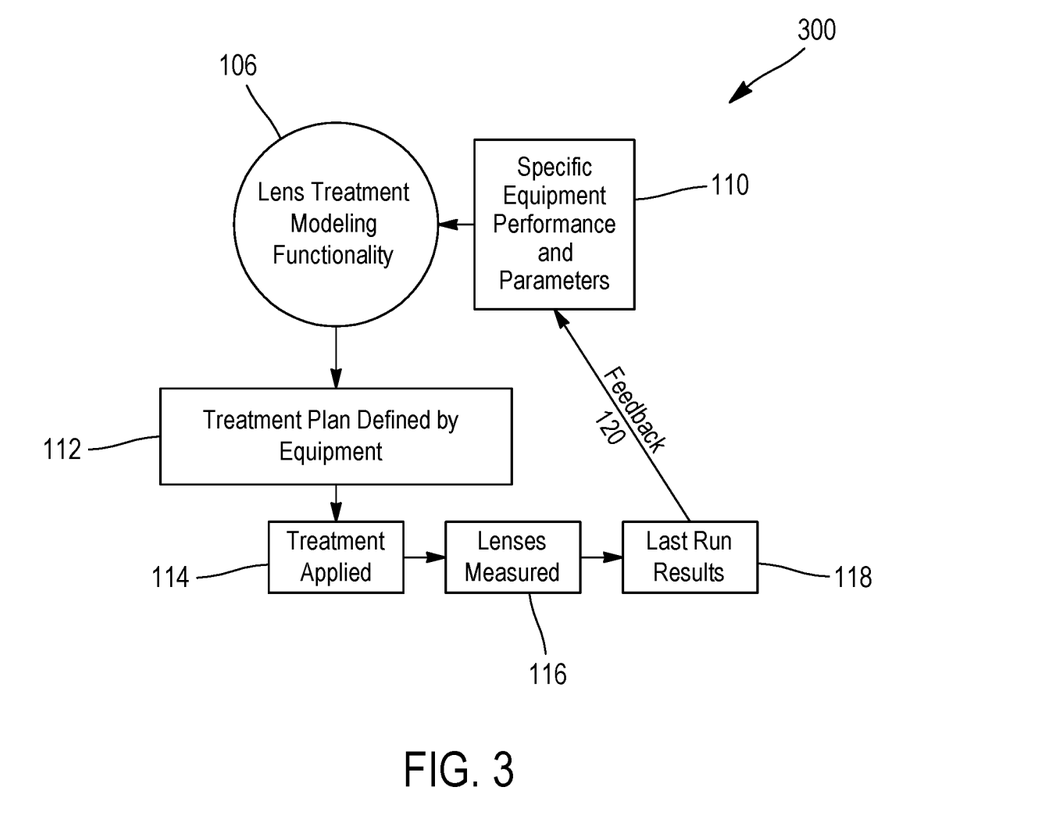
FIG. 3 is block diagram of feedback loop control, such as may, by way of example, be employed in the system and process of FIG. 1, according to various embodiments.

FIG. 3 is block diagram for feedback loop control 300 such as may, by way of example, be employed in the system and process of FIG. 1, according to various embodiments, and as illustrated. As noted, last run results 118 may be fed back, such as along illustrated path 120 to provide further performance and parameters 110 of equipment 108 to ophthalmic lens treatment modeling functionality 106. In accordance with such embodiments of the present systems and methods, lens(es) resulting from application of the ophthalmic lens treatment plan 114 may be measured at 116 to provide such last run results. Last run results 118 may include, by way of example, one or more of a measure of the treated lens' spectral performance including reflection, transmission and absorption characteristics as well as spectral parameters, product performance testing results of the treated lens, results of a cosmetic inspection of the treated lens, a measured light through the treated lens, adhesion of the treatment(s) to the lens, resulting scratch resistance of the treated lens, resulting abrasion resistance of the treated lens, chemical resistance of the treated lens, and/or the like.

As discussed herein, performance and parameters 110 of equipment 108 may be considered in optimizing lens coatings. For example, such optimization may involve a feasibility check based on machine capability and/or maintenance status. In particular performance and parameters 110 of equipment 108 may include, whether the equipment includes of employs various tools or tooling, for example whether an electron beam gun can be used, any sputter target employed for deposition of coatings, use of evaporation boats by the equipment, use of an ion gun, use of shields, use of distribution masks, sector geometry employed by the equipment; and/or the like. Additionally, as noted, such optimization feasibility check may include machine maintenance status, or the like, such as condition of ion gun filaments, condition of specific components within the electron beam gun or the ion gun, cleanliness of shields, age of coating material to be used, condition of tooling, age of chemicals to be used, condition of chemicals to be used, age of dye bath, dye bath temperature, room conditions etc. As also noted, last run results that may be affected by machine capability and/or maintenance status may be considered in ophthalmic lens treatment plan determinations, for example optimization may take into account resulting optical thickness measurement(s), measured resulting lens axis orientation, resulting lens color, and/or the like. Such last run results that may be affected by machine capability and/or maintenance status may be considered in addition to, or in place of, the last run results discussed above. Hence, as noted, lens treatment plan 112 may, in accordance with various embodiments of the present systems and methods, be defined not only by equipment 108 available to apply the lens treatments, but also the performance and parameters 110 of such equipment.

Although, the present systems and methods provide greater customization of lens treatments than typical batch processing, various embodiments of the present systems and methods, may make use of batch processing when applicable. For example, optimizing selection of ophthalmic lens treatments for the given lens or pair of lenses may call for application of one or more ophthalmic lens treatments that may be carried out using batch processes. That is, when optimizing application of ophthalmic lens treatments for the given lens or pair of lenses can include inclusion of the given lens or pair of lenses in at least one batch processing for a ophthalmic lens treatment, modeling functionality 106 may in accordance with such various embodiments of the present systems and methods, select such batch processing for at least one particular lens treatment, where such batch processing will not compromise the optimization of the customer ordered ophthalmic lens treatments.

Figure 4:
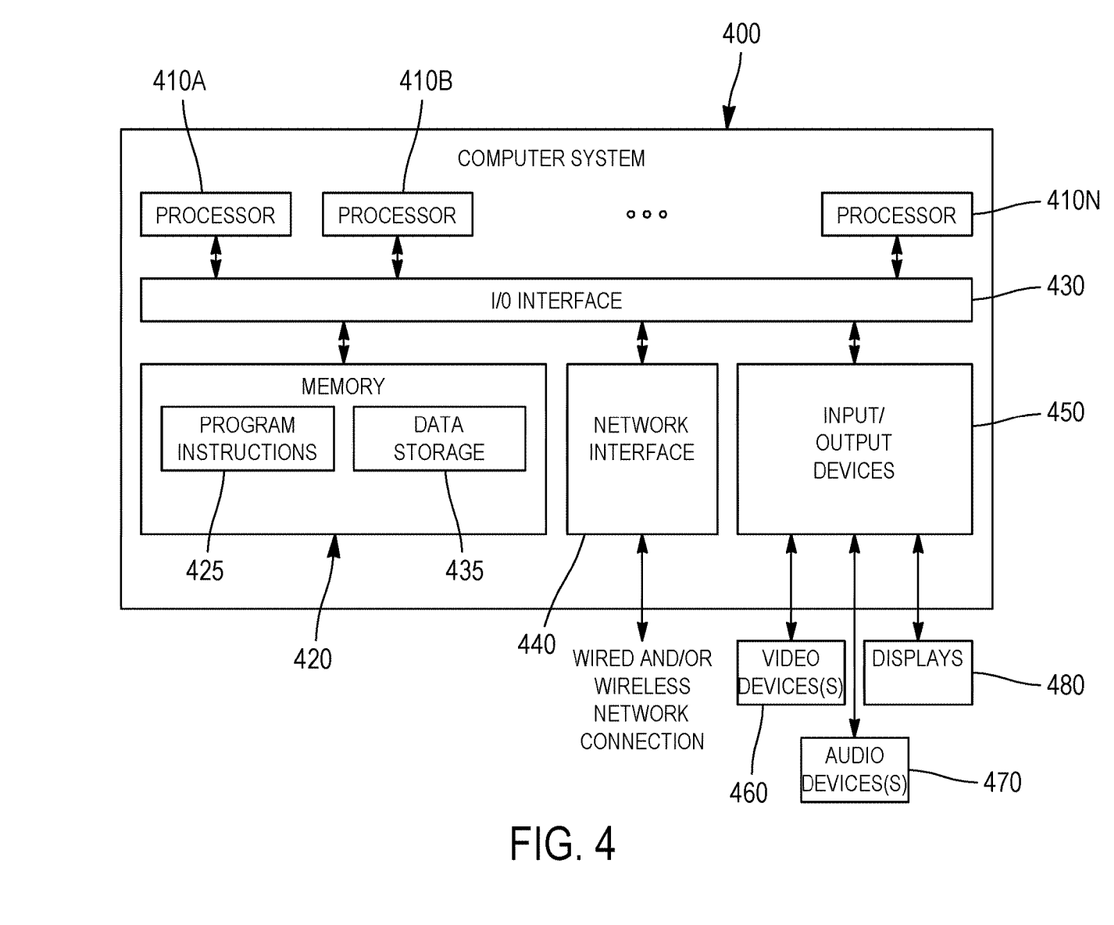
FIG. 4 is a block diagram of a computer system, device, station, or terminal configured to implement various ophthalmic lens treatment planning techniques disclosed herein, according to some embodiments.

Embodiments of the present systems and methods for optimization of the selection and application of ophthalmic lens treatments, as described herein, may be implemented or executed, at least in part, by one or more computer systems. One such computer system is illustrated in FIG. 4. In various embodiments, computer system 400 may be a server, a mainframe computer system, a workstation, a network computer, a desktop computer, a laptop, a tablet computing device, media player, or the like. For example, in some cases, computer 400 may implement one or more steps of example processes (100) described above with respect to FIGS. 1 through 3, and/or a computer system such as computer system 400 may be used as, or as part of, one or more of a special purpose ophthalmic lens treatment panning system, a centralized control systems for lens treatment equipment, and/or may be a computer system implementing embodiments of the present methods, and/or the like. In various embodiments two or more of these computer systems may be configured to communicate with each other in any suitable way, such as, for example, via a network.

As illustrated, example computer system 400 includes one or more processors 410 (i.e. 410A through 410N) coupled to a system memory 420 via an input/output (I/O) interface 430. Example computer system 400 further includes a network interface 440 coupled to I/O interface 430, and one or more input/output devices 450, such as video device(s) 460 (e.g., a camera), audio device(s) 470 (e.g., a microphone and/or a speaker), and display(s) 480. Computer system 400 may also include a cursor control device (e.g., a mouse or touchpad), a keyboard, etc. Multiple input/output devices 450 may be present in computer system 400 or may be distributed on various nodes of computer system 400. In some embodiments, similar input/output devices may be separate from computer system 400 and may interact with one or more nodes of computer system 400 through a wired or wireless connection, such as over network interface 440.

In various embodiments, computer system 400 may be a single-processor system including one processor 410, or a multi-processor system including two or more processors 410 (e.g., two, four, eight, or another suitable number). Processors 410 may be any processor capable of executing program instructions. For example, in various embodiments, processors 410 may be general-purpose or embedded processors implementing any of a variety of instruction set architectures (ISAs), such as the x86, POWERPC®, ARM®, SPARC®, or MIPS® ISAs, or any other suitable ISA. In multi-processor systems, each of processors 410 may commonly, but not necessarily, implement the same ISA. Also, in some embodiments, at least one processor 410 may be a graphics processing unit (GPU) or other dedicated graphics-rendering device.

System memory 420 may be configured to store program instructions and/or data accessible by processor 410. In various embodiments, system memory 420 may be implemented using any suitable memory technology, such as static random access memory (SRAM), synchronous dynamic RAM (SDRAM), nonvolatile/Flash-type memory, or any other type of memory. As illustrated, program instructions and data implementing certain operations, such as, for example, those described in connection with FIGS. 1 through 3, above, may be stored within system memory 420 as program instructions 425 and data storage 435, respectively. In other embodiments, program instructions and/or data may be received, sent or stored upon different types of computer-accessible media or on similar media separate from system memory 420 or computer system 400. Generally speaking, a computer-readable medium may include any tangible or non-transitory storage media or memory media such as magnetic or optical media—e.g., disk or CD/DVD-ROM coupled to computer system 400 via I/O interface 430, Flash memory, random access memory (RAM), etc. Program instructions and data stored on a tangible computer-accessible medium in non-transitory form may further be transmitted by transmission media or signals such as electrical, electromagnetic, or digital signals, which may be conveyed via a communication medium such as a network and/or a wireless link, such as may be implemented via network interface 440.

In some embodiments, I/O interface 430 may be configured to coordinate I/O traffic between processor 410, system memory 420, and any peripheral devices in the device, including network interface 440 or other peripheral interfaces, such as input/output devices 450. In some embodiments, I/O interface 430 may perform any suitable protocol, timing or other data transformations to convert data signals from one component (e.g., system memory 420) into a format usable by another component (e.g., processor 410). In some embodiments, I/O interface 430 may include support for devices attached through various types of peripheral buses, such as a variant of the Peripheral Component Interconnect (PCI) bus standard or the Universal Serial Bus (USB) standard, for example. In some embodiments, the function of I/O interface 430 may be split into two or more separate components, such as a north bridge and a south bridge, for example. In addition, in some embodiments, some or all of the functionality of I/O interface 430, such as an interface to system memory 420, may be incorporated into processor 410.

Network interface 440 may be configured to allow data to be exchanged between computer system 400 and other devices attached to a network, such as other computer systems, or between nodes of computer system 400. In various embodiments, network interface 440 may support communication via wired or wireless general data networks, such as any suitable type of Ethernet network, for example; via telecommunications/telephony networks such as analog voice networks or digital fiber communications networks; via storage area networks such as Fiber Channel SANs, or via any other suitable type of network and/or protocol.

As shown in FIG. 4, memory 420 may include program instructions 425, configured to implement certain embodiments described herein, and data storage 435, comprising various data accessible by program instructions 425. In an embodiment, program instructions 425 may include software elements corresponding to one or more of the various embodiments illustrated in the above figures. For example, program instructions 425 may be implemented in various embodiments using any desired programming language, scripting language, or combination of programming languages and/or scripting languages (e.g., C, C++, C#, JAVA®, JAVASCRIPT®, PERL®, etc.). Data storage 435 may include data that may be used in these embodiments. In other embodiments, other or different software elements and data may be included.

A person of ordinary skill in the art will appreciate that computer system 400 is merely illustrative and is not intended to limit the scope of the disclosure described herein. In particular, the computer system and devices may include any combination of hardware or software that can perform the indicated operations. Additionally, the operations performed by the illustrated components may, in some embodiments, be performed by fewer components or distributed across additional components. Similarly, in other embodiments, the operations of some of the illustrated components may not be provided and/or other additional operations may be available. Accordingly, systems and methods described herein may be implemented or executed with other computer system configurations.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:
1. A method comprising:
receiving, in an ophthalmic lens treatment planning system, lens and ophthalmic lens treatment information from a customer lens order, identification of equipment to apply one or more ophthalmic lens treatments from the customer order, and performance and parameters of the equipment;
formulating, by the ophthalmic lens treatment planning system, an optimal ophthalmic lens treatment plan to be implemented by the equipment wherein formulating the optimal ophthalmic lens treatment plan comprises applying computer-based models to the plan employing possible combinations of ophthalmic lens treatments that can be applied to the lens employing the equipment;
applying the one or more ophthalmic lens treatments from the customer order to the lens for implementing the optimal ophthalmic lens treatment plan by the equipment;

accepting measurements of a resulting lens, following application of the optimal ophthalmic lens treatment plan to the lens, to develop last run results;

feeding back the last run results to the ophthalmic lens treatment planning system to provide further performance and parameters of the equipment to the ophthalmic lens treatment planning system; and applying an ophthalmic lens treatment to a lens for a subsequent lens order based upon the feeding back of the last run results that provided the further performance and parameters of the equipment.

2. The method of claim 1, wherein developing the last run results comprise measuring one or more of the following:

a measure of lens spectral performance including reflection, transmission and absorption characteristics;

spectral parameters;

product performance testing;

cosmetic inspection;

treatment adhesion;

scratch resistance abrasion resistance; and chemical resistance.

3. The method of claim 1, wherein formulating an optimal ophthalmic lens treatment plan comprises:

considering aspects of a given lens or pair of lenses relevant to ophthalmic lens treatments for the given lens or pair of lenses; and considering and optimizing the optimal ophthalmic lens treatment plan by optimizing the performance and parameters of the equipment.

4. The method of claim 1, wherein the at least one ophthalmic lens treatment includes an anti-reflective coating, and formulating an optimal ophthalmic lens treatment plan comprises optimizing one or more of the following: anti-reflective coating layer thicknesses, application rates, ramps, soaks, ion gun power, gas flow, gas pressure, e-gun voltage, distribution mask size, distribution mask location, lens fixture, and application process for the equipment and the performance and parameters of the equipment.

5. The method of claim 1, wherein the at least one ophthalmic lens treatment includes a hard coating, and formulating an optimal ophthalmic lens treatment plan comprises optimizing one or more of the following: hard coating thickness, type, cure rate, cure type, tooling, lens preparation process, lens stripping process, and treatment application process for the equipment and the performance and parameters of the equipment.

6. The method of claim 1, wherein the at least one ophthalmic lens treatment includes tinting, and formulating an optimal ophthalmic lens treatment plan comprises optimizing one or more of the following: tinting temperature, color, one or more treatment dyes to use, time, pre-processing, post-processing, gradient parameters, tint applicator parameters, and dye application process for the equipment and the performance and parameters of the equipment.

7. The method of claim 1, wherein the performance and parameters of the equipment comprise use of one or more of the following: an electron beam gun, any sputter target employed for deposition of coatings, use of evaporation boats, use of an ion gun, condition of filaments, condition of specific components within the electron beam gun or the ion gun, use of shields, cleanliness of shields, use of distribution masks, sector geometry employed by the equipment, resulting optical thickness measurement, resulting lens axis orientation, resulting lens color, age of coating material to be used, condition of tooling, age of chemicals to be used, condition of chemicals to be used, age of dye bath, dye bath temperature, and room conditions for the equipment.

8. The method of claim 1, wherein the ophthalmic lens treatment information includes information about one or more of the following: lens coatings, lens tints, lens films, lens polarization, and lens photochromic properties.

9. The method of claim 1, wherein the ophthalmic lens treatment information comprises information about techniques for applying treatments to the lens.

10. The method of claim 1, wherein the ophthalmic lens treatment information comprises information about hard multi-coat lens treatments.

11. The method of claim 1, wherein the optimal ophthalmic lens treatment plan includes application of at least one ophthalmic lens treatment using a batch process.

12. An ophthalmic lens treatment system comprising:

equipment to apply one or more ophthalmic lens treatments; and an ophthalmic lens treatment planning system comprising at least one processor and a memory coupled to the at least one processor, the memory configured to store program instructions executable by the at least one processor to cause the ophthalmic lens treatment planning system to:

receive lens and ophthalmic lens treatment information from a customer lens order;

receive identification of the equipment to apply the ophthalmic lens treatment from the customer lens order;

receive performance and parameters of the equipment; and formulate an optimal ophthalmic lens treatment plan to be implemented by the equipment to apply one or more ophthalmic lens treatments from the customer lens order to the lens, wherein formulation of the optimal ophthalmic lens treatment plan comprises applying computer-based models to the plan employing possible combinations of ophthalmic lens treatments that can be applied to the lens employing the equipment;

apply the one or more ophthalmic lens treatments from the customer lens order to the lens for implementing the optimal ophthalmic lens treatment plan by the equipment accept measurements of a resulting lens, following application of the optimal ophthalmic lens treatment plan to the lens, to develop last run results;

feedback the last run results to the ophthalmic lens treatment planning system to provide further performance and parameters of the equipment to the ophthalmic lens treatment planning system; and apply an ophthalmic lens treatment to a lens for a subsequent lens order based upon the feeding back of the last run results that provided the further performance and parameters of the equipment.

* * * * *